United States Patent [19]

Ramanadin et al.

[11] Patent Number: 4,462,937
[45] Date of Patent: Jul. 31, 1984

[54] PROCESS FOR THE PREPARATION OF TRIFLUOROMETHYLBENZENES FROM THE CORRESPONDING TRICHLORO- OR TRIBROMO-METHYLBENZENES

[75] Inventors: Ramanadin, Ales; Laurent Seigneurin, Salindres, both of France

[73] Assignee: Rhone-Poulenc Industries, Paris, France

[21] Appl. No.: 243,205

[22] Filed: Mar. 12, 1981

[30] Foreign Application Priority Data

Mar. 17, 1980 [FR] France ............... 80 05877

[51] Int. Cl.³ .............. C07C 51/04; C07C 17/20
[52] U.S. Cl. .............. 260/544 F; 260/544 D; 570/127; 570/145
[58] Field of Search ............... 570/127, 145; 260/544 F, 544 D

[56] References Cited

U.S. PATENT DOCUMENTS

| | | | |
|---|---|---|---|
| 1,967,244 | 7/1934 | Holt et al. | 570/145 |
| 2,181,554 | 11/1939 | Kracker et al. | 260/544 |
| 3,859,372 | 1/1975 | Robota | 570/145 |
| 3,966,832 | 6/1976 | Lademann et al. | 260/651 F |
| 4,183,873 | 1/1980 | Baxamusa et al. | 570/145 |
| 4,242,286 | 12/1980 | Ohsaka | 570/145 |

FOREIGN PATENT DOCUMENTS

| | | |
|---|---|---|
| 1618390 | 12/1970 | Fed. Rep. of Germany . |
| 2756235 | 7/1978 | Fed. Rep. of Germany ...... 570/145 |
| 2137744 | 12/1972 | France . |
| 2295004 | 7/1976 | France . |

*Primary Examiner*—Thomas A. Waltz

[57] ABSTRACT

This invention relates to a continuous process for the preparation of trifluoromethylbenzenes from the corresponding trichloro- or tribromo-methylbenzenes with hydrofluoric acid. The process is characterized by passing an ascending stream of gaseous hydrofluoric acid, countercurrently through a plurality of mobile successive liquid layers of the trichloro- or tribromo-methylbenzenes.

11 Claims, 1 Drawing Figure

PROCESS FOR THE PREPARATION OF TRIFLUOROMETHYLBENZENES FROM THE CORRESPONDING TRICHLORO- OR TRIBROMO-METHYLBENZENES

TECHNICAL FIELD OF INVENTION

The present invention relates to a process for the preparation of trifluoromethylbenzenes from the corresponding trichloro- or tribromo-methylbenzenes. More particularly, it relates to a continuous reaction of trichloro- or tribromomethylbenzenes with hydrofluoric acid to produce the corresponding trifluoromethylbenzenes.

BACKGROUND ART

In the present invention, the term "trifluoromethylbenzene" includes benzene compounds that have at least one and possibly more trifluoromethyl-substituents.

One prior art process for the preparation of derivatives of benzene containing at least one trifluoromethyl group is described in U.S. Pat. No. 3,966,832. In accordance with that process, an autoclave is precharged with hydrofluoric acid alone or in homogeneous admixture with trichloromethylbenzene and hydrochloric acid to a pressure of at least 20 atmospheres (all pressures herein are absolute) in order to minimize the danger of an explosion, caused by too rapid an increase in pressure, upon starting the reaction. Trichloromethylbenzene and hydrofluoric acid are then introduced continuously into the autoclave under a pressure of more than 20 atmospheres; the hydrofluoric acid being in an excess of the required stoichiometric amount by at least 25 mole percent. After the reaction mixture has reached a given height, the liquid mixture is either withdrawn from the autoclave at a rate corresponding to the rate of feed, or else the mixture is passed into one or more additional autoclaves and withdrawn from the last autoclave of the cascade series. The initial autoclave and any autoclaves in the cascade are maintained at a temperature of between 80° C. and 150° C. throughout the process.

In order to obtain a sufficiently homogeneous mixture, as is necessary for proper operation of a continuous process, the reaction must usually be conducted at an autoclave pressure of 30 to 50 atmospheres. It is plain that operation under such pressures, particularly in an autoclave cascade or series arrangement, requires complex and costly equipment and procedures. Moreover, applicant has found that the required autoclave pressure is even further increased by the number of substituents present on the benzene ring of the trichloromethylbenzene starting material. This increase in required autoclave pressure is particularly important in the preparation of the various herbicides that comprise trifluoromethylbenzene having one or more chloro- substituents on the benzene ring. Therefore, in those important industrial processes the above-mentioned expense and complexity of equipment are magnified.

Another disadvantage inherent in this prior art process is the large excess of hydrofluoric acid which must be used in the process to achieve high product yield. As a result, the product mixture contains a large amount of unreacted hydrofluoric acid. This remaining acid must therefore be removed from the product and for any economic operation of the process be recycled to the feed of the initial autoclave. Again, these purification and recycle processes and procedures disadvantage the prior art process in time, in economics and in size and complexity of equipment required for its operation.

DISCLOSURE OF THE INVENTION

It is accordingly an object of this invention to provide a process that substantially overcomes the aforementioned drawbacks of the prior art process.

This object and other additional objects and advantages of this invention, apparent from the detailed description and claims which follow, are accomplished in accordance with this invention by an improved continuous process for the preparation of trifluoromethylbenzenes from the corresponding trichloro- or tribromo-methylbenezenes with hydrofluoric acid. This improved process is conducted by passing an ascending stream of gaseous hydrofluoric acid, countercurrently through a plurality of mobile successive liquid layers of the corresponding trichloro- or tribromo- methylbenzenes.

Moreover, in accordance with one preferred embodiment of this invention, the process is carried out with a molar ratio of hydrofluoric acid to trichloro- or tribromomethylbenzene between about 3 and about 4. Even more preferably, this ratio is between about 3 and 3.5.

BEST MODE FOR CARRYING OUT THE INVENTION

Figure 1:
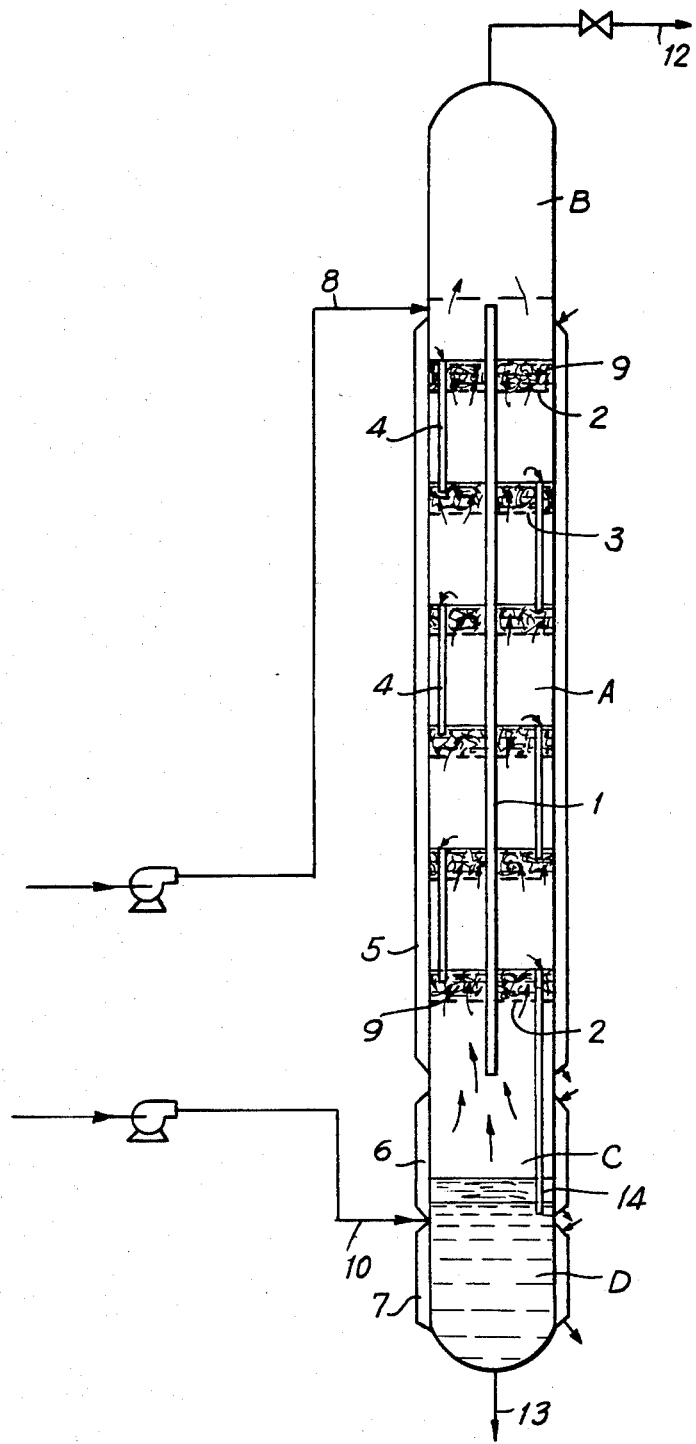
FIG. 1 is a sectional view of a reactor, illustrating one embodiment of a process of this invention for preparing trifluoromethylbenzenes from tribromo- and trichloromethylbenzenes with hydrofluoric acid.

The improved process for preparing trifluoromethylbenzenes from the corresponding trichloro- or tribromo-methylbenzenes with hydrofluoric acid is characterized by the step of passing an ascending stream of gaseous hydrofluoric acid, countercurrently through a plurality of mobile successive liquid layers of the trichloro- or tribromo-methylbenzenes. Preferably the molar ratio of hydrofluoric acid to trichloroor tribromo-methylbenzene is between about 3 and 4 and more preferably between about 3 and 3.5.

The number of mobile liquid layers and height of each layer are preferably selected in such a manner that the gaseous hydrofluoric acid stream, after it has passed through the last liquid layer, contains primarily hydrochloric acid and is practically free of hydrofluoric acid and so that the liquid coming from the first liquid layer traversed by the gaseous hydrofluoric acid contains primarily the desired trifluoromethylbenzene derivative and is practically free of the corresponding trichloro- or tribromo-methylbenzene derivative. This dual objective can be even more closely controlled by modifying the molar ratio of the hydrofluoric acid to the trichloro- or tribromo-methylbenzene during the course of the process while staying within the above-indicated limits. It is plain that such modifications, in view of the teachings and disclosures herein, are within the skill of the art.

The rate of flow of the reagents—hydrofluoric acid and trichloro- or tribromo- methylbenzenes—is preferably adjusted in such a manner that the total contact time (defined as the ratio of the volume of liquid in the various liquid layers to the rate of feed of the trichloro- or tribromomethylbenzene) between the gaseous hydrofluoric acid and the liquid methylbenzenes is between about 10 and 100 minutes. Even more preferably, the contact time is between about 15 and 75 minutes. Again, it is plain that such flow rate adjustment, in view of the teachings and disclosures herein, is within the skill of the art.

The inventive process may advantageously be carried out at a temperature between about 80° and 150° C., and preferably between about 90° and 120° C. In general, the process is carried out at a pressure greater than about 5 atmospheres, preferably at a pressure between about 5 and 20 atmospheres, and most preferably between about 8 and 15 atmospheres.

It is therefore plain that this invention makes it possible, to operate at pressures that are very substantially lower than those which characterized and disadvantaged the prior art processes and to use considerably lower amounts of hydrofluoric acid, while at the same time obtaining the desired trifluoromethylbenzenes in yields of more than 95%. The process of this invention furthermore makes it possible to obtain in separate streams the desired trifluoromethylbenzenes and the hydrochloric acid by-product. Therefore, subsequent treatments of the reaction products and the complex equipment associated with such treatments are much simplified and recycle of hydrofluoric acid is avoided.

The invention is more particularly directed to the preparation of trifluoromethylbenzenes of the general formula:

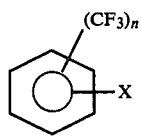

from corresponding trichloro- or tribromo-methylbenzenes of the formulas:

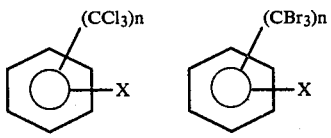

wherein X represents at least one substituent which is inert under the reaction conditions, such as for example H, Cl, F, Br, COF or CF$_3$, at least one substituent which is transformable in accordance with a known procedure under the conditions of the reaction, such as COCl or COBr (which are transformed, as is known, into COF) or combinations thereof, and n is an integer that is greater than or equal to 1 and preferably equal to 1 or 2.

Examples of trifluoromethylbenzenes which can be prepared by the processes of this invention are trifluoromethylbenzene, 3-chloro-trifluoromethylbenzene, 4-chlorotrifluoromethylbenzene, 3,4-dichloro-trifluoromethylbenzene, 3-fluoro-trifluoromethylbenzene, para-bromo-trifluoromethylbenzene, para-fluoro-trifluoromethylbenzene, meta-bistrifluoromethylbenzene, para-bis-trifluoromethylbenzene, meta-trifluoromethylbenzoyl fluoride and ortho-trifluoromethylbenzoyl fluoride.

Referring now to FIG. 1, one embodiment of a process of this invention is depicted. This embodiment comprises a reaction column A, a de-bubbling column B, a hydrofluoric acid still C, and a settler D.

The depicted reaction column A contains a plurality of plates 2, fixed on a shaft 1 and having a plurality of openings of small diameter 3. Each plate is traversed by a pipe 4. The column A, the still C and the settler D are provided with double jackets 5, 6 and 7, each of which contains a heat-exchange fluid, whose flow aides in maintaining the desired temperatures of the portion which they surround.

The liquid trichloro- or tribromo-methylbenzene derivative is introduced continuously at 8. The liquid initially forms a liquid layer on the upper-most of plates 2. When the level of the liquid on that plate reaches the height of the upper end of the pipe 4, thereby forming first layer 9, the liquid flows down pipe 4 and onto the second plate 2 where, in a similar fashion a second liquid layer 9 is formed, and so on down to the lower-most of plates 2.

Simultaneous with the introduction of the trichloro- or tribromo-methylbenzene derivative, liquid hydrofluoric acid is introduced continuously at 10. The acid is then vaporized in still C where, the temperature is maintained between about 80° C. and 150° C. by the flow of heat exchange fluid in jacket 6. The gaseous hydrofluoric acid thus formed traverses, countercurrently to the liquid flow, liquid layers 9, passing through openings 3 in plates 2. The actual size of openings 3 is determined by the pressure of the gas stream so that the liquid is maintained above the plate by the simple pressure of the gas.

After having passed through all of the liquid layers, the gas, which now consists essentially of hydrochloric acid, flows into de-bubbling column B where it is separated from any entrained liquid. When the pressure in B reaches the value desired, the gaseous hydrochloric acid is released through the valve 11 and is passed continuously via 12 into a conventional rectification stage (not shown in FIG. 1).

The liquid flowing from the lower-most liquid layer 9, which consists essentially of the desired trifluoromethylbenzene derivative, is collected in settler D (through pipe 4). In settler D, substantially all of the small amount of hydrofluoric acid, which may be entrained in the trifluoromethylbenzene derivative, separates out from the desired product and forms an upper-layer 14 on that product. The separated hydrofluoric acid is then vaporized together with the hydrofluoric acid which is introduced at 10 during the continuous process.

The product of the reaction—a trifluoromethylbenzene derivative—is withdrawn continuously through outlet 13. It usually contains a very small proportion of the starting trichloro- or tribromo-methylbenzene derivative. These are separated and the desired product purified in conventional distillation stages (not shown in FIG. 1).

As has been stated above, the number of liquid layers, the volume of liquid in any layer and the rates of flow of the reagents are adjusted in such a manner so as to minimize the presence of hydrofluoric acid in the outlet gases at 12 and the presence of trichloro- or tribromomethylbenzene derivatives in the liquid at outlet 13. Therefore, it should be understood that the arrangement depicted in FIG. 1 is for illustration purposes only. And, the number of layers, the distance between any two adjacent liquid layers 9, the size of openings 3, volume of liquid layers 9 or the like may be modified in accordance with the teachings herein.

In order to describe further the present invention, the following examples are set forth. These examples are primarily for the purposes of illustration and any specific enumeration therein should not be construed as a limitation; this invention being solely defined by the claims appended hereto.

EXAMPLE 1

Preparation of trifluoromethylbenzene $C_6H_5$-$CF_3$ from trichloromethylbenzene $C_6H_5$-$CCl_3$ The reaction of this Example is conducted in an apparatus such as shown in FIG. 1—column A having a height of 3 m and a diameter of 6.5 cm, having 15 equally distributed plates 2, and each plate having 31 holes of 2 mm diameter, distributed uniformly in the shape of a square circumscribed by the plate. 870 g/h (43.5 moles/h) of liquid hydrofluoric acid and 2820 g/h of technical trichloromethylbenzene (containing 2737 g of pure trichloromethylbenzene) (14 moles/h) were introduced into reaction column A as shown in FIG. 1 and described above. The hydrofluoric acid was vaporized in still C, which was maintained at a temperature of 90°–92° C., and passed through the 15 liquid layers, each layer having a liquid height of 6 cm. A pressure of 9 atmospheres and a temperature of 90° to 92° C. was maintained in the column A.

2110 g/h of a liquid organic mixture were withdrawn from outlet 13. Analysis of this mixture afforded the following composition by weight:
- $C_6H_5CF_3$: 95.5%
- $C_6H_5CF_2Cl$: 1.3%
- $C_6H_5CFCl_2$: 0.25%
- $C_6H_5CCl_3$: 0.002% the balance consisting of impurities from the reactants. The analysis of this product corresponds to a molar yield of $C_6H_5CF_3$ with respect to the $C_6H_5CCl_3$ of 95.7% and to a fluorination rate:

$$\frac{\text{number of atoms of fluorine fixed on the } CCl_3 \text{ group}}{\text{number of substitutable chlorine atoms}} \times 100 = 99.45\%$$

At outlet 12 there was also collected a gas containing 3.9 mole percent of hydrofluoric acid and 96.08 mole percent of hydrochloric acid.

EXAMPLE 2

Preparation of para-chloro-trifluoromethylbenzene p-$ClC_6H_4CF_3$ from para-chloro-trichloromethylbenzene p-$ClC_6H_4CCl_3$ Into the same apparatus as described in Example 1, there were introduced 3220 g/h (14 moles/h) of pure p-$ClC_6H_4CCl_3$ and 890 g/h (49 moles/h) of liquid hydrofluoric acid. The temperature in the apparatus was maintained at 110° C. and the pressure at 14.5 atmospheres.

2530 g/h of an organic liquid mixture were collected from outlet 13. This mixture contained (by weight):
- p-$ClC_6H_4CF_3$: 98.5%
- p-$ClC_6H_4CF_2Cl$: 1.4%
- p-$ClC_6H_4CFCl_2$: 0.07% the balance consisting of traces of p-$ClC_6H_4CCl_3$ and impurities from the reactants. The molar yield of p-$ClC_6H_4CF_3$ with respect to the p-$ClC_6H_4CCl_3$ was 98.6%. The fluorination rate, as defined in Example 1, was 99.5%. At outlet 12 there was also collected a gas containing 14.7 mole percent of hydrofluoric acid and 85.3 mole percent of hydrochloric acid.

EXAMPLE 3

Preparation of 3,4-dichloro-trifluoromethylbenzene from 3,4-dichloro-trichloromethylbenzene Into the same apparatus as in Example 1, there were charged 3703 g/h (14 moles/h) of 3,4-dichloro-trichloromethylbenzene (previously purified) and 900 g/h (4.5 moles/h) of liquid hydrofluoric acid. The apparatus was maintained at a temperature of 120° C. and a pressure of 15 atmospheres.

2385.5 g/h of an organic liquid mixture were collected from outlet 13. The mixture contains (by weight):
- 3,4-$Cl_2C_6H_3CF_3$: 97.5%
- 3,4-$Cl_2C_6H_3CF_2Cl$: 1.62%
- 3,4-$Cl_2C_6H_3CFCl_2$: 0.8%
- 3,4-$Cl_2C_6H_3CCl_3$: 0.08%

The molar yield of 3,4-$Cl_2C_6H_3CF_3$ with respect to 3,4-$Cl_2C_6H_3CCl_3$ was 98.34%. The fluorination rate was 99.36%. A gas containing 92.74 mole percent of hydrochloric acid and 7.25 mole percent of hydrofluoric acid was also collected at outlet 12.

EXAMPLE 4

Preparation of ortho-trifluoromethylbenzoyl fluoride $CF_3C_6H_4COF$ from ortho-trichloromethylbenzoyl chloride $CCl_3C_6H_4COCl$ 3612 g/h (14 moles/h) of liquid $CCl_3C_6H_4COCl$ and 1240 g/h (62 moles/h) of liquid hydrofluoric acid were introduced into the same apparatus as in Example 1.

The apparatus was maintained at a temperature of 100° C. and at a pressure of 15 atmospheres. 2695 g/h of a liquid organic mixture were collected from outlet 13. The mixture had a composition (by weight) as follows:
- $CF_3C_6H_4COF$: 96.9%
- $CF_2ClC_6H_4COF$: 3.0% plus traces of $CFCl_2C_6H_4COF$ and $CCl_3C_6H_4COF$. The molar yield in $CF_3C_6H_4COF$ with respect to $CCl_3C_6H_4COCl$ was 97.14%. The fluorination rate was 99%. A gas containing 89.6 mole percent of hydrochloric acid and 10.3 mole percent of hydrofluoric acid was also collected at outlet 12.

While we have herein before presented a number of embodiments of our invention, it is apparent that our basic construction and process can be altered to provide other embodiments which utilize our invention. Thus, it will be appreciated that the scope of our invention is to be defined by the claims appended hereto rather than the specific embodiment which have been presented hereinbefore by way of example.

We claim:

1. A process for the preparation of a trifluoromethylbenzene from the corresponding trichloro- or tribromomethylbenzene with hydrofluoric acid comprising passing an ascending stream of gaseous hydrofluoric acid countercurrently through a plurality of separate mobile successive liquid layers of the trichloro- or tribromomethylbenzene at a temperature between about 80° C. and 150° C. in the absence of catalyst.

2. The process according to claim 1, wherein the temperature is maintained between about 90° C. and 120° C.

3. The process according to claim 1, wherein the pressure is maintained at more than about 5 atmospheres.

4. The process according to claim 3 wherein said pressure is between about 5 atmospheres and 20 atmospheres.

5. The process according to claim 4 wherein said pressure is between about 8 atmospheres and 15 atmospheres.

6. The process according to claim 1 wherein the molar ratio of hydrofluoric acid to trichloro- or tribromomethylbenzene is between about 3 and 4.

7. The process according to claim 6 wherein said molar ratio is between about 3 and 3.5.

8. The process according to claim 1 wherein the ratio of the total volume of said liquid layers to the rate of feed of the trichloro- or tribromomethylbenzene is between about 10 and about 100.

9. The process according to claim 8 wherein said ratio is between about 15 and about 75.

10. The process according to claim 1 wherein said trifluoromethylbenzene is selected from the group of trifluoromethylbenzenes having the formula:

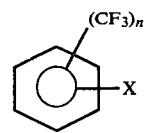

wherein x represents at least one substituent selected from the group consisting of H, Cl, F, Br, COF, $CF_3$, COCl, COBr and combinations thereof, and n is an integer that is greater than or equal to 1.

11. The process according to claim 10 wherein n is 1 or 2.